(12) United States Patent
Alisi et al.

(10) Patent No.: US 8,415,476 B2
(45) Date of Patent: *Apr. 9, 2013

(54) INDAZOLE HAVING ANALGESIC ACTIVITY

(75) Inventors: Maria Alessandra Alisi, Rome (IT); Nicola Cazzolla, Abano Laziale (IT); Guido Furlotti, Rome (IT); Angelo Guglielmotti, Rome (IT); Lorenzo Polenzani, Grottaferrata (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 511 days.

This patent is subject to a terminal disclaimer.

(21) Appl. No.: 12/638,470

(22) Filed: Dec. 15, 2009

(65) Prior Publication Data
US 2010/0094015 A1    Apr. 15, 2010

Related U.S. Application Data

(62) Division of application No. 10/549,930, filed as application No. PCT/EP2004/004390 on Apr. 23, 2004, now Pat. No. 7,662,836.

(30) Foreign Application Priority Data

May 15, 2003    (IT) .............................. MI2003A0972

(51) Int. Cl.
*C07D 211/26*    (2006.01)
(52) U.S. Cl.
USPC ....................................................... 546/229
(58) Field of Classification Search ................... 546/229
See application file for complete search history.

(56) References Cited

U.S. PATENT DOCUMENTS

| | | | |
|---|---|---|---|
| 5,654,320 A | 8/1997 | Catlow et al. | 514/322 |
| 6,017,931 A | 1/2000 | Silverman et al. | 514/318 |
| 6,096,476 A | 8/2000 | Yanagida et al. | 430/270.1 |
| 6,096,746 A | 8/2000 | Suzuki et al. | 514/254.06 |
| 6,197,769 B1 | 3/2001 | Alisi et al. | 514/234.5 |
| 6,770,650 B2 | 8/2004 | Gong et al. | 514/253.01 |

FOREIGN PATENT DOCUMENTS

| | | |
|---|---|---|
| EP | 908 459 | 4/1999 |
| EP | 975 623 | 2/2000 |
| WO | 98/07728 | 2/1998 |
| WO | 98/46589 | 10/1998 |
| WO | 03/004026 | 1/2003 |

OTHER PUBLICATIONS

Patani et al. "Bioisosterism: A rational . . . " Chem. Rev. v.96, p. 3147-3176 (1996).*
Peglion et al. "Preparation of . . . " CA136:209939 (2002).*
Rubini et al. "Synthesis of isosteric . . . " Tetrhedron v.42, p. 6039-06045 (1986).*
U.S. Appl. No. 12/607,463, filed Oct. 28, 2009, Alisi, et al.
Schaus, et al., "Synthesis and structure-activity relationships . . . " J. Med. Chem.. v. 41, p. 1943-1955 (1998).
Englen, et al., "Central 5HT4 receptors" Trends in pharmacol. sci. v. 16(1111) p. 391-398 (1995).
Alisi, et al., "preparation of indazoleamide . . . " CA 129:316219 (1998).
Catlow, et al., "Preparation of indazolecarboxamides . . . " Ca 127:205575 (1997).
Patani, et al., "bioisosterism: a rational approach in drug design" Che. Rev. v. 96, p. 3147-3176 (1996).
Michael A. Ashburn et al, "Management of chronic pain", The Lancet, vol. 353, pp. 1865-1869 May 29, 1999.
Edited by Patrick D. Wall et al, Textbook of Pain, 4$^{th}$ edition, Churchill Livingstone 1999.
Joachim Scholz et al., "Can we conquer pain?", Nature Neuroscience Supplement, vol. 5, pp. 1062-1067 2002.
John D. Prugh et al., "A simple method of protecting a secondary amine with tert butyloxycarbonyl (boc) in the presence of a primary amine", Synthetic Communications, vol. 22, No. 16, pp. 2357-2360 1992.
Charles E. Kwartler et al, "The preparation of sulfanilamidoindazoles", J.A.C.S., vol. 65, pp. 1804-1806 1943.
Giorgio Corsi et al., "1-Halobenzyl-1H-indazole-3-carboxylic acids. A new class of antispermatogenic agents", Journal of Medicinal Chemistry, vol. 19, No. 6, pp. 778-783 1976.
Aloke K. Dutta et al., "Structure-activity relationship studies of novel 4-[2-[bis(4-fluorophenyl)methoxy]ethyl]-1-(3-phenylpropyl)piperidine analogs: synthesis and biological evaluation at the dopamine and serotonin Transporter Sites", Journal of Medicinal Chemistry, vol. 39, No. 3, pp. 749-756 1996.
Richard F. Smith et al., "Diindazolo[2,3-a, 2',3'-d]pyrazine-7,14-dione", J.O.C., vol. 23, p. 621 1958.
Nicolo Vivona et al., "Mononuclear heterocyclic rearrangements. part 12 (1). rearrangement of 1,2,4-oxadiazoles into indazoles", Journal of Heterocyclic Chemistry, vol. 16, pp. 783-784 1979.
N.P. Buu-Hoi et al., "Indazole-3-carboxylic acids and their derivatives", Journal of Heterocyclic Chemistry, vol. 1, No. 5, pp. 239-241 1964.
Richard C. Larock, "Comprehensive organic transformations", VCH, pp. 965-966, (1989).
Lowell O. Randall et al., "A method for measurement of analgesic activity on inflamed tissue", Arch. Int. Pharmacodyn. Ther., vol. 111, No. 4, pp. 409-419 1957.

(Continued)

*Primary Examiner* — Celia Chang
(74) *Attorney, Agent, or Firm* — Oblon, Spivak, McClelland, Maier & Neustadt, L.L.P.

(57) ABSTRACT

An intermediate of formula (II)

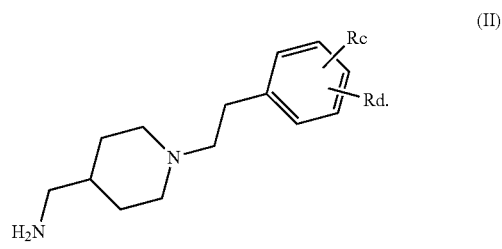

28 Claims, No Drawings

OTHER PUBLICATIONS

David Andrew et al., "Mechanical and heat sensitization of cutaneous nociceptors after peripheral inflammation in the rat", Neurophysiol, vol. 82, No. 5, pp. 2649-2656 1999.

K. Hargreaves, et al., "A new and sensitive method for measuring thermal nociception in cutaneous hyperalgesia", Pain, vol. 32 pp. 77-88 1988.

C. Courteix et al., "Streptozocin-induced diabetic rats: behavioural evidence for a model of chronic pain", Pain, vol. 53, pp. 81-88 1993.

A. W. Bannon et al., "ABT-594, a novel cholinergic channel modulator, is efficacious in nerve ligation and diabetic neuropathy models of neuropathic pain", Brain Research, vol. 801, pp. 158-163 1998.

* cited by examiner

INDAZOLE HAVING ANALGESIC ACTIVITY

The present application is a divisional of U.S. Ser. No. 10/549,930, filed on Sep. 20, 2005, which is a National Stage (371) of PCT/EP04/04390, filed on Apr. 23, 2004, which claims priority to Italian Application No. MI2003A 000972, filed on May 15, 2003.

The present invention relates to an indazole having analgesic activity, a method for the preparation thereof and a pharmaceutical composition containing the same.

Chronic pain is very widespread. On average about 20% of the adult population suffers from it, and it is generally associated with clinical conditions characterized by chronic and/or degenerative lesions.

Typical examples of pathologies characterized by chronic pain are rheumatoid arthritis, osteoarthritis, fibromyalgia, neuropathies, etc. [Ashburn M A, Staats P S. Management of chronic pain. Lancet 1999; 353: 1865-69].

Chronic pain is often debilitating and is the cause of loss of the capacity for work and poor quality of life. Therefore it also has adverse economic and social consequences.

The analgesic drugs currently used in the treatment of chronic pain belong basically to two classes: the non-steroidal anti-inflammatory drugs (NSAIDs), which combine analgesic activity and anti-inflammatory activity, and the opioid analgesics. These classes constitute the basis for the three-step "analgesic scale" suggested by the World Health Organization for drug treatment of pain [Textbook of Pain. 4th edition. PD Wall and R Melzack Eds. Churchill Livingstone, 1999].

Chronic pain is notoriously difficult to treat using the treatments currently available. Consequently the development of new analgesics has always been one of the main aims of the pharmaceutical industry. Nevertheless, despite the extensive research efforts directed towards identifying a suitable analgesic compound, there is a significant number of patients whose pain condition is still not being adequately treated [Scholz J, Woolf C J. Can we conquer pain? Nat Neusci. 2002; 5: 1062-76].

Surprisingly, it has now been found that such properties are possessed by a new family of indazoles.

In its first aspect, the present invention thus relates to an indazole of general formula:

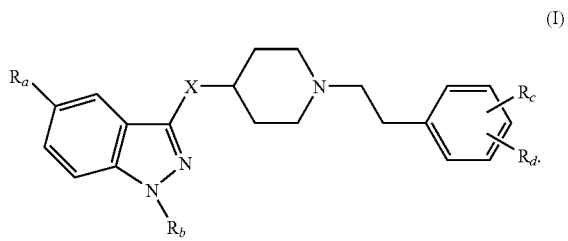

(I)

where

X is $C(O)NHCH_2$, $NHC(O)$ or $NHC(O)CH_2$;

$R_a$ is H, $NH_2C(O)$, $CH_3C(O)NH$, $CH_3SO_2$, $CH_3SO_2NH$, linear or branched $C_1$-$C_3$ alkyl, linear or branched $C_1$-$C_3$ alkoxy, or halogen;

$R_b$ is H, linear or branched $C_1$-$C_6$ alkyl; aryl-($C_1$-$C_3$)alkyl optionally substituted with 1 or 2 halogen atoms, with a $C_1$-$C_3$ alkyl group or a $C_1$-$C_3$ alkoxy group;

and in which a) when X is $C(O)NHCH_2$ $R_c$ is hydroxy, amino, di-($C_1$-$C_3$)alkyl-amino, tri-($C_1$-$C_3$) alkyl-ammoniomethyl, nitro, trifluoromethyl, nitrile, $CH_3C(O)NH$, $CH_3SO_2NH$, $CH_3SO_2$, R'R"$NSO_2$, where R' and R" are H, or a linear or branched $C_1$-$C_6$ alkyl, $R_d$ is H, hydroxy, amino, di-($C_1$-$C_3$)alkyl-amino, tri-($C_1$-$C_3$)alkyl-ammoniomethyl, nitro, trifluoromethyl, nitrile, $CH_3C(O)NH$, $CH_3SO_2NH$, $CH_3SO_2$, R'R"$NSO_2$, where R' and R" have the meanings stated above, with the proviso, however, that when $R_a$ and $R_d$ are both H, and $R_b$ is isopropyl, then $R_c$ is not hydroxy;

b) when X is $NHC(O)$ or $NHC(O)CH_2$ $R_c$ and $R_d$, which may be equal or different, are H, hydroxy, $C_1$-$C_3$ alkoxy, halogen, amino, di-($C_1$-$C_3$)alkylamino, tri-($C_1$-$C_3$)alkyl-ammoniomethyl, nitro, trifluoromethyl, nitrile, $CH_3C(O)NH$, $CH_3SO_2NH$, $CH_3SO_2$, R'R"$NSO_2$, where R' and R" have the meanings stated above, and their acid addition salts with pharmaceutically acceptable organic and inorganic acids.

Typical examples of pharmaceutically acceptable acids are: oxalic, maleic, methanesulphonic, paratoluenesulphonic, succinic, citric, tartaric, lactic, hydrochloric, phosphoric, sulphuric.

Preferred meanings of $R_a$ are H and $C_1$-$C_3$ alkyl.

Preferred meanings of $R_b$ are H and $C_1$-$C_3$ alkyl.

Preferred meanings of $R_c$ are H, $NO_2$, $NH_2$, OH and $C_1$-$C_3$ alkoxy.

The preferred meaning of $R_d$ is H.

The analgesic activity of the compounds of formula (I) was found by means of two experimental models in the rat: mechanical hyperalgesia induced by CFA and mechanical hyperalgesia in diabetic neuropathy induced by streptozocin.

As is known to a person skilled in the art, the aforementioned experimental models can be regarded as predictive of activity in man.

CFA-induced hyperalgesia is a syndrome characterized by the activation of circuits with the task of controlling the inflammatory response and associated with the appearance of conditions that interfere with the perception of pain. Injection of CFA is in fact capable of peripherally inducing the release of specific substances (mediators of the inflammatory response and algogenic agents) responsible for local damage and centrally, at the level of the spinal cord, determining biochemical changes that support the amplification of the perception of pain. As is well known, this model constitutes a valid tool for investigating drugs for use in the treatment of inflammatory pain in man and, in particular, in the control of conditions such as hyperalgesia and allodynia.

Typical examples of human pathologies characterized by this type of pain associated with degenerative inflammatory processes are rheumatoid arthritis and osteoarthritis.

In its turn, the diabetic neuropathy induced by streptozocin in the rat represents an insulin-dependent syndrome characterized by a concomitant decrease in the conduction velocity of the motor and sensory nerves and the appearance of a number of anomalies in pain perception. As is well known, this experimental model constitutes a useful tool for the investigation of drugs for use in the treatment of neuropathic pain in man. In particular, the model represents a valid example of a whole host of neuropathic pains characterized by phenomena such as hyperalgesia and allodynia following primary lesions or dysfunctions of the nervous system. Typical examples of human pathologies characterized by dysfunctions of this type and by the presence of neuropathic pain are diabetes, cancer, immunodeficiency diseases, trauma, ischaemias, multiple sclerosis, sciatic neuralgias, neuralgia of the trigeminal nerve and post-herpetic syndromes.

In a second aspect, the present invention relates to a method of preparation of a compound of formula (I) in which X═C(O)NHCH$_2$ and acid addition salts thereof with pharmaceutically acceptable organic or inorganic acids, characterized in that it comprises the following stages:

a) reaction of an amine of formula (II)

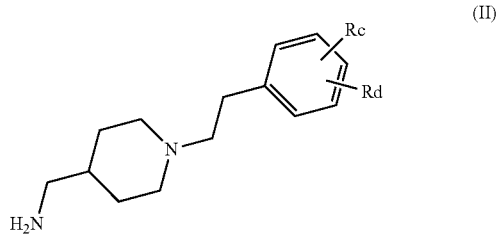

where

R$_c$ and R$_d$ have the same meanings as stated above or, when R$_c$ or

R$_d$ is an amino or alcoholic group, R$_c$ and R$_d$ may be an amino or alcoholic group protected by a protective group of conventional type, with a derivative of an indazole-carboxylic acid of formula (IIIa)

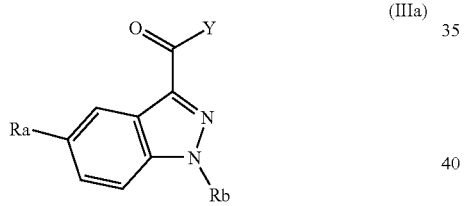

where

R$_a$ and R$_b$ have the meanings stated above, and

Y is a Cl or Br atom, or an OR or OC(O)R group, where R is a linear or branched alkyl having from 1 to 6 carbon atoms, or with a derivative of an indazole-carboxylic acid of formula (IIIb)

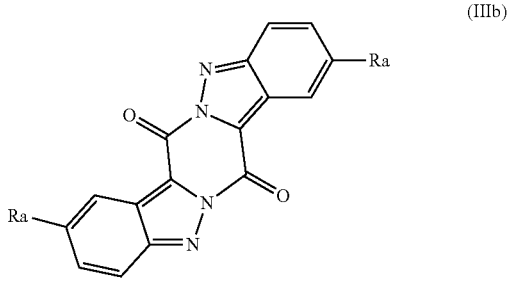

where

R$_a$ has the meanings stated above, b) cleavage of any possible protective group of the aforesaid amino or alcoholic group, and c) optional formation of an acid addition salt of the indazoleamide of formula (I) with a pharmaceutically acceptable organic or inorganic acid.

In a third aspect, the present invention relates to a method of preparation of a compound of formula (I) in which X═NH(CO) or NH(CO)CH$_2$ and acid addition salts thereof with pharmaceutically acceptable organic or inorganic acids, characterized in that it comprises the following stages:

a') reaction of an amine of formula (IV)

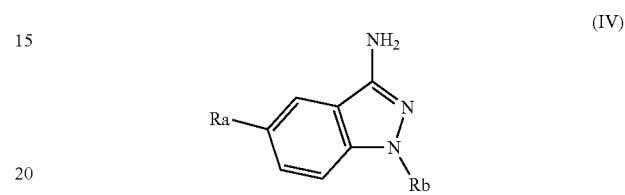

where

R$_a$ and R$_b$ have the meanings stated above, is condensed with a derivative of a carboxylic acid of formula (V)

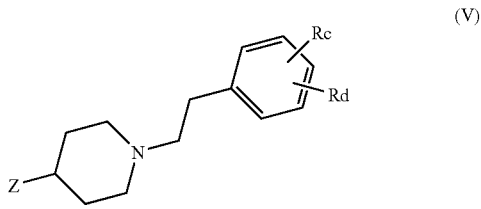

where

R$_c$ and R$_d$ have the same meanings as stated above or, when R$_c$ or R$_d$ is an amino or alcoholic group, R$_c$ and R$_d$ may be an amino or alcoholic group protected by a protective group of conventional type, and Z is a group C(O)Y or CH$_2$C(O)Y in which Y is a Cl or Br atom, or an OR or OC(O)R group, where R is a linear or branched alkyl having from 1 to 6 carbon atoms, b') cleavage of any possible protective group of the aforesaid amino or alcoholic group, and c') optional formation of an acid addition salt of the indazoleamide of formula (I) with a pharmaceutically acceptable organic or inorganic acid.

A person skilled in the art will easily understand that some compounds of formula (I) can also be prepared from another compound of formula (I) by conventional techniques. For example, when R$_c$ and/or R$_d$ are an NO$_2$ group the latter can be reduced to give the corresponding compound of formula (I) in which R$_c$ and/or R$_d$ are NH$_2$.

The amine of formula (II) may be obtained according to conventional methods. For example, by alkylation of isonipecotamide with a suitable halide and then reduction of the amide to primary amine (WO 9807728) or by protection of aminomethylpiperidine with benzaldehyde (Synthetic Communications 22(16), 2357-2360, 1992), alkylation with a suitable halide and deprotection.

The intermediate of formula (II) in which R$_c$ and R$_d$ have the meanings stated above is novel. This intermediate therefore is another aspect of the present invention.

The compounds of formula (IIIa) and (IIIb) may also be obtained according to conventional methods. For example, the compounds of formula (IIIa) in which Y is chlorine may be obtained from the corresponding acid with thionyl chloride (J. Med. Chem., 1976, Vol. 19 (6), pages 778-783), whereas the compounds of formula (IIIa) in which Y is OR or OC(O)R may be obtained by means of known reactions of esterification or of formation of mixed anhydrides (R. C. Larok, Comprehensive Organic Transformations, VCH, pages 965-966). In their turn, the compounds of formula (IIIb) may be obtained according to J.O.C. 1958, Vol. 23 page 621.

In their turn the compounds of formula (IV) may be obtained according to the conventional methods described in the literature, for example in J. of Heterocyclic Chemistry 1979 (16) 783-784, or in J.A.C.S., 1943 (65) 1804-1806.

The compounds of formula (V) may also be obtained according to conventional methods. For example, the compounds of formula (V) in which Y is chlorine may be obtained by saponification of the corresponding esters followed by treatment with thionyl chloride.

Preferably, stages (a) and (a') are carried out by reacting
a compound of formula (II) with a compound of formula (IIIa) in which Y is chlorine, or
a compound of formula (II) with a compound of formula (IIIb), or
a compound of formula (IV) with a compound of formula (V) in which Y is chlorine,
in the presence of a suitable diluent and at a temperature of from 0 to 140° C., for a time of from 0.5 to 20 hours.

Preferably, the reaction temperature is of from 15 to 40° C. Advantageously, the reaction time is of from 1 to 18 hours.

Preferably the diluent is aprotic, polar or nonpolar. Even more preferably it is aprotic nonpolar. Examples of suitable aprotic nonpolar diluents are the aromatic hydrocarbons, e.g. toluene. Examples of suitable aprotic polar diluents are dimethylformamide and dimethylsulphoxide.

In the embodiments in which a compound of formula (II) is reacted with a compound of formula (IIIa) in which Y is chlorine, or in which a compound of formula (IV) is reacted with a compound of formula (V) in which Y is chlorine, the aforesaid stages (a) and, respectively, (a') are preferably carried out in the presence of an organic or inorganic acceptor of acids.

Examples of suitable organic acceptors of acids are pyridine, triethylamine and the like. Examples of suitable inorganic acceptors of acids are alkali carbonates and bicarbonates.

In stages (b) and (b'), cleavage of the protective group of the amino or alcoholic group is preferably carried out by techniques known in the chemistry of protective groups.

In their turn, stages (c) and (c') are preferably preceded by a stage of isolation of the indazoleamide of formula (I).

In a further aspect, the present invention relates to a pharmaceutical composition containing an effective amount of a compound of formula (I), or of an addition salt thereof with a pharmaceutically acceptable acid, and at least one pharmaceutically acceptable inert ingredient.

A typical example of a pathologic state that might benefit from treatment with a pharmaceutical composition according to the present invention is chronic pain. Typically this chronic pain is due to chronic lesions or to degenerative processes such as rheumatoid arthritis, osteoarthritis, fibromyalgia, oncologic pain, neuropathic pain and the like.

Preferably, the pharmaceutical compositions of the present invention are prepared in a suitable dosage form.

Examples of suitable dosage forms are tablets, capsules, coated tablets, granules, solutions and syrups for oral administration; creams, ointments and medicated patches for topic administration; suppositories for rectal administration and sterile solutions for injectable, aerosol or ophthalmic administration.

Advantageously, these dosage forms will be formulated in such a way as to provide controlled release over time of the compound of formula (I) or of a salt thereof with a pharmaceutically acceptable acid. Indeed, depending on the type of treatment, the required time of release may be very short, normal or protracted.

The dosage forms may also contain other conventional ingredients such as: preservatives, stabilizers, surfactants, buffers, salts for the regulation of the osmotic pressure, emulsifiers, sweetener agents, coloring agents, flavouring agents and the like.

Moreover, when required by particular therapies, the pharmaceutical composition of the present invention may contain other pharmacologically active ingredients whose concomitant is therapeutically useful.

The amount of the compound of formula (I) or of the pharmaceutically acceptable acid salt thereof in the pharmaceutical composition of the present invention may vary in a wide range depending on known factors, such as for example the type of disease to be treated, the severity of the disease, the patient's body weight, the dosage form, the chosen route of administration, the number of daily administrations and the efficacy of the chosen compound of formula (I). However, the optimum amount may be easily and routinely determined by a person skilled in the art.

Typically, the amount of the compound of formula (I) or of a salt thereof with a pharmaceutically acceptable acid in the pharmaceutical composition of the present invention will be such that it ensures an administration level of from 0.001 to 100 mg/kg/day. Even more preferably, of from 0.1 to 10 mg/kg/day.

The dosage forms of the pharmaceutical composition of the present invention can be prepared according to techniques that are well known to the pharmaceutical chemist and comprise mixing, granulation, compression, dissolution, sterilization and the like.

The following examples will illustrate the invention, without limiting it in any way.

In the following examples, the substituents on the aromatic ring ($R_c$ and $R_d$) are indicated with numbering in bold.

EXAMPLE 1

(N((1-(2-(4-nitrophenyl)ethyl)-4-piperidinyl)methyl)-1H-indazole-3-carboxamide hydrochloride (AF3R298)

(I, $R_a$=$R_b$=$R_d$=H; $R_c$=4-NO$_2$; X=C(O)NHCH$_2$)

a) N-hexahydro-4-pyridinylmethyl-N-phenylmethylidene-amine

Benzaldehyde (4.6 g; 0.044 mol) was added dropwise to a solution of 4-aminomethylpiperidine (5.0 g; 0.044 mol) in toluene (20 ml). The solution thus obtained was stirred for 3 h at room temperature. Then the solvent was removed by evaporation at reduced pressure and the residue was taken up twice with toluene to give the desired product that was used as such without further purification.

b) 1-(2-(4-nitrophenyl)ethyl)-4-piperidinylmethane-amine

The product of Example 1a) (8.8 g; 0.044 mol) was dissolved in absolute ethanol (50 ml) and added to a suspension containing 2-(4-nitrophenyl)ethylbromide (10.0 g; 0.044 mol) and anhydrous potassium carbonate (12.1 g; 0.088 mol) in absolute ethanol (100 ml). The suspension thus obtained was boiled under reflux for 16 hours. The reaction mixture was then left to cool to room temperature and filtered. The filtrate was evaporated at reduced pressure. The residue thus obtained was then suspended in 3N HCl (50 ml) and stirred for 3 h at room temperature. The solution was then transferred to a separatory funnel and the acid aqueous phase was washed with ethyl acetate (4×50 ml), the aqueous phase was then made alkaline by addition of 6N NaOH and extracted with dichloromethane. The organic phase was dried over $NaSO_4$ and the solvent was removed by evaporation at reduced pressure to give the desired product (9 g).

$^1$H-NMR (δ, CDCl3+D2O): 1.43-1.50 (m, 3H); 1.76 (d J=12 Hz, 2H); 2.03 (t, J=12 Hz, 2H); 2.67-2.52 (m, 4H); 2.82-3.06 (m, 4H); 7.39 (d, J=9 Hz, 2H); 8.12 (d, J=9 Hz, 2H); 7.95 (quintet, J=1 Hz, 1H).

c) —N((1-(2-(4-nitrophenyl)ethyl)-4-piperidinyl)methyl)-1H-indazole-3-carboxamide hydrochloride A solution of the product of Example 1b) (8.4 g; 0.032 mol) in toluene (85 ml) was added, using a dropping funnel, to a suspension containing 7H,14H-indazole(2',3':4,5)pyrazine (1,2-b)indazole-7,14,dione (4.6 g; 0.016 mol) prepared as described in J.O.C., 1958, Vol. 23, page 621, in toluene (60 ml). The reaction mixture was stirred at room temperature for 38 hours and then filtered. The solid was separated and added to a stirred saturate solution of $NaHCO_3$ (200 ml) for 2 h. The reaction mixture was filtered and the thus obtained solid product was converted into the corresponding hydrochloride by dissolution in absolute ethanol, addition of hydrogen chloride in ethanol and recrystallization from ethanol, to give the desired product (4.2 g).

m.p.: 251-252.5° C.

Elemental analysis for $C_{22}H_{25}N_5O_3$·HCl

|  | C | H | N |
|---|---|---|---|
| Found % | 59.60 | 5.96 | 15.77 |
| Calculated % | 59.52 | 5.90 | 15.78 |

$^1$H-NMR (δ, DMSO): 1.52-2.11 (m, 5H); 2.85-302 (m, 2H); 3.17-3.64 (m, 8H); 7.19-7.28 (m, 1H); 7.36-7.46 (m, 1H); 7.53-7.56 (m, 3H); 8.13-8.26 (m, 3H); 8.55 (t, J=6 Hz, 1H); 10.82 (s broad, 1H); 13.70 (s, 1H).

EXAMPLE 2

N((1-(2-(4-aminophenyl)ethyl)-4-piperidinyl)methyl)-1H-indazole-3-carboxamide dihydrochloride (AF3R02)

(I, $R_a$=$R_b$=$R_d$=H, $R_c$=4-$NH_2$, X=C(O)NHCH$_2$)

A solution of the product of Example 1c) in the form of base (3 g; 0.007 mol) in 95° ethanol (200 ml) was hydrogenated on 10% Pd—C (0.3 g) at 40 psi for 3 hours. The mixture was then filtered and the filtrate was concentrated at reduced pressure. The thus obtained product was crystallized from ethyl acetate and transformed into the corresponding hydrochloride by dissolution in a mixture of ethyl acetate:ethanol=9:1 and addition of hydrogen chloride in ethanol to give the desired product (1.2 g).

m.p.: 271-273° C. (decomp.)

Elemental analysis for $C_{22}H_{27}N_5O$·2HCl·½$H_2O$

|  | C | H | N |
|---|---|---|---|
| Found % | 57.31 | 6.68 | 15.05 |
| Calculated % | 57.52 | 6.58 | 15.24 |

$^1$H-NMR (δ, DMSO+$D_2O$): 1.45-1.66 (m, 2H); 1.80-2.00 (m, 3H); 2.86-3.14 (m, 4H); 3.19-3.35 (m, 4H); 3.46-3.80 (m, 2H+HDO); 7.22-7.35 (m, 3H); 7.35-7.49 (m, 3H); 7.64 (d, J=9 Hz; 1H); 8.17 (d, J=9 Hz, 1H).

EXAMPLE 3

N((1-(2-(4-nitrophenyl)ethyl)-4-piperidinyl)methyl)-1-(1-methylethyl)-1H-indazole-3-carboxamide oxalate (AF3R306)

(I, $R_a$=$R_d$=H, $R_b$=i-$C_3H_7$, $R_c$=4-$NO_2$, X=C(O)NHCH$_2$)

1-(1-methylethyl)-1H-indazole-3-carboxylic acid chloride (2.45 g; 0.011 mol), prepared as described in EP-B1-0 975 623, was added portionwise to a solution of product 1b) (3.0 g; 0.011 mol) and of triethylamine (4.6 ml; 0.033 mol) in toluene (50 ml). The mixture was stirred at room temperature for 18 h. The solvent was removed by evaporation at reduced pressure. The residue was taken up with 1N NaOH and dichloromethane. The mixture was transferred to a separately funnel. The organic phase was separated and dried over $Na_2SO_4$. The solvent was removed by evaporation at reduced pressure and the residue thus obtained was purified by flash chromatography, eluting with ethyl acetate to give the desired product (5.5 g) which was then transformed into the corresponding oxalate by dissolution in ethyl acetate, addition of a stoichiometric amount of oxalic acid and recrystallization from ethyl acetate:ethanol=9:1, twice, to give the desired salt (3.5 g).

m.p.: 98° C. (decomp.)

Elemental analysis for $C_{25}H_{31}N_5O_3$·C2H2O4·½$H_2O$

|  | C | H | N |
|---|---|---|---|
| Found % | 59.27 | 6.15 | 12.72 |
| Calculated % | 59.11 | 6.25 | 12.77 |

$^1$H-NMR (δ, DMSO+$D_2O$): 1.55 (d, J=7 Hz, 6H); 1.44-1.66 (m, 2H); 1.83-2.02 (m, 3H); 2.98 (t, J=12 Hz, 2H); 3.10-3.40 (m, 6H); 3.55 (d, J=12 Hz, 2H); 5.07 (heptet, J=7 Hz, 1H); 7.28 (t, J=8 Hz, 1H); 7.46 (t, J=7 Hz, 1H); 7.59 (d, J=9 Hz; 2H); 7.79 (d, J=8 Hz; 1H); 8.11-8.26 (m, 3H); 8.42 (t, J=6 Hz, 1H).

EXAMPLE 4

N((1-(2-(4-aminophenyl)ethyl)-4-piperidinyl)methyl)-1-(1-methylethyl)-1H-indazole-3-carboxamide dihydrochloride (AF3R294)

(I, $R_a=R_d=H$, $R_b=i-C_3H_7$, $R_c=4-NH_2$, $X=C(O)NHCH_2$)

A solution of the product of Example 3, in the form of base, (2.7 g; 0.006 mol) in 95° ethanol (30 ml) was hydrogenated on 10% Pd—C (0.27 g) at 40 psi for 5 hours. The mixture was then filtered and the filtrate was concentrated at reduced pressure. The product thus obtained was transformed into the corresponding hydrochloride by dissolution in ethyl acetate, addition of hydrogen chloride in ethanol and recrystallization from a mixture of ethyl acetate:ethanol=8:2, to give the desired product (1.4 g).

m.p.: 278° C. (decomp.)

Elemental analysis for $C_{25}H_{33}N_5O.2HCl H_2O$

|  | C | H | N |
|---|---|---|---|
| Found % | 59.05 | 7.42 | 13.63 |
| Calculated % | 58.82 | 7.31 | 13.72 |

$^1$H-NMR (δ, DMSO): 1.55 (d, J=7 Hz, 6H); 1.45-2.13 (m, 5H); 2.80-3.64 (m, 10H); 5.08 (heptet, J=7 Hz, 1H); 7.20-7.49 (m, 6H); 7.79 (d, J=9 Hz; 1H); 8.18 (d, J=9 Hz, 1H) 8.39 (t, J=6 Hz, 1H); 9.15-11.18 (m, 4H)

EXAMPLE 5

N-(1-methyl-1H-indazol-3-yl)-1-(2-phenylethyl)piperidine-4-carboxamide hydrochloride (AF3R334)

(I, $R_a=R_c=R_d=H$, $R_b=CH_3$, $X=NHC(O)$)

a) 1-(2-phenylethyl)-4-piperidine-carboxylic acid hydrochloride

A suspension of 1-(2-phenylethyl)-4-carbetoxypiperidine (12.2 g, 0.047 mol) obtained as described in J. Med. Chem. 1996 (39), 749-756, in 1N NaOH (100 ml) was heated under reflux for 4 h. After cooling to room temperature, the solution was made acid with 6N HCl to pH 2, concentrated by evaporation at reduced pressure, and the solid thus obtained was filtered and dried in a stove under vacuum to give the desired product (12.1 g), $^1$H-NMR (δ, DMSO+D$_2$O): 1.79-2.19 (m, 4H); 2.43-3.74 (m, 9H); 7.18-7.41 (m, 5H);

b) 1-(2-phenylethyl)-4-piperidinecarbonyl chloride hydrochloride

A suspension of the product of Example 5a) (2.0 g; 0.007 mol) and of thionyl chloride (0.81 ml; 0.011 mol) in toluene (20 ml) was heated under reflux for 3 h. The solvent was then removed by evaporation at reduced pressure and the residue was taken up with toluene (2×20 ml) to give the desired product (2.2 g) that was used as such without further purification.

c) N-(1-methyl-1H-indazol-3-yl)-1-(2-phenylethyl)piperidine-4-carboxamide hydrochloride The product of Example 5b) (1.68 g; 0.006 mol) was added to a solution of 1-methyl-1H-3-indazoleamine (0.86 g; 0.006 mol), prepared as described in the Journal of Heterocyclic Chemistry 1979 (16), 783-784, and of triethylamine (2.4 ml; 0.018 mol) in toluene (20 ml). The reaction mixture was stirred at room temperature for 18 h and then the solvent was removed by evaporation at reduced pressure. The residue thus obtained was taken up with 1N NaOH and dichloromethane and transferred to a separatory funnel. The organic phase was separated, dried over Na$_2$SO$_4$ and the solvent was removed by evaporation at reduced pressure. The product thus obtained was transformed into the corresponding hydrochloride by dissolution in ethanol, addition of hydrogen chloride in ethanol and recrystallization from ethanol, to give the desired salt (1.6 g).

m.p.: 235-237° C.

Elemental analysis for $C_{22}H_{26}N_4O.HCl¼H_2O$

|  | C | H | N |
|---|---|---|---|
| Found % | 65.71 | 6.80 | 13.73 |
| Calculated % | 65.50 | 6.87 | 13.89 |

$^1$H-NMR (δ, DMSO D2O): 1.91-2.27 (m, 4H) 2.70-3.42 (m, 7H); 3.63-3.75 (m, 2H); 3.96 (s, 3H); 7.10 (t, J=8 Hz, 1H); 7.22-7.46 (m; 6H); 7.56 (d, J=8 Hz, 1H) 7.74 (d, J=8 Hz, 1H); 10.51 (s, 1H)

EXAMPLE 6

N-(1-methyl-1H-indazol-3-yl)-1-(2-(4-methoxyphenyl)ethyl)piperidine-4-carboxamide hydrochloride (AF3R328)

(I, $R_a=R_d=H$, $R_b=CH_3$, $R_c=4-OCH_3$, $X=NHC(O)$)

a) 1-(2-(4-methoxyphenyl)ethyl)-4-piperidine-carboxylic acid hydrochloride

The title product was obtained (15.8 g) by working in a similar way to that described in Example 5a) but starting from 1-(2-(4-methoxyphenyl)ethyl)-4-carbetoxypiperidine (16.5 g; 0.057 mol), prepared as described in U.S. Pat. No. 6,017,931, instead of from 1-(2-phenylethyl)-4-carbetoxypiperidine.

$^1$H-NMR (δ, DMSO): 1.80-2.17 (m, 4H); 2.41-3.74 (m, 7H); 3.73-(s, 3H); 6.89 (d, J=9 Hz, 2H); 7.19 (d, J=9 Hz, 2H) 11.00 (s broad, 1H); 12.53 (s broad, 1H)

b) 1-(2-(4-methoxyphenyl)ethyl)-4-piperidinecarbonyl chloride hydrochloride

The title product was obtained (14.2 g) starting from the product of Example 6a) (13.8 g; 0.048) and by working in a similar way to that described in example 5b). The product thus obtained was used as such without further purification.

c) N-(1-methyl-1H-indazol-3-yl)-1-(4-methoxyphenyl)ethyl)piperidine-4-carboxamide hydrochloride The title product was obtained (9.2 g) starting from the product of Example 6b) (14.2 g; 0.045 mol) and from 1-methyl-1H-3-indazoleamine (6.6 g; 0.045 mol) and by working in a way similar to that described in Example 5c). A mixture of ethyl acetate:ethanol 9:1 was used as the crystallization solvent.

m.p.: 137-139° C. (decomp.)

Elemental analysis for $C_{23}H_{28}N_4O_2 \cdot HCl H_2O$

|  | C | H | N |
|---|---|---|---|
| Found % | 61.80 | 7.14 | 12.45 |
| Calculated % | 61.80 | 6.99 | 12.53 |

$^1$H-NMR (δ, DMSO): 1.95-2.25 (m, 4H) 2.69-3.48 (m, 7H); 3.57-3.70 (m, 2H); 3.74 (s, 3H); 3.96 (s, 3H); 6.92 (d, J=9 Hz, 2H); 7.08 (t, J=9 Hz, 1H); 7.20 (d, J=9 Hz, 2H); T38 (t, J=8 Hz, 1H); 7.56 (d, J=9 Hz, 1H); 7.76 (d, J=8 Hz, 1H); 10.36-11.07 (m, 2H)

EXAMPLE 7

N-(1-methyl-1H-indazol-3-yl)-1-2-4-hydroxyphenyl)ethyl)piperidine-4-carboxamide hydrochloride (AF3R330)

(I, $R_a=R_d=H$, $R_b=CH_3$, $R_c=4$-OH, X=NHC(O))

A solution of the product of Example 6c) (6.7 g; 0.017 mol) in dichloromethane (300 ml) was added dropwise to a solution of BBr$_3$ (8.5 g; 0.034 mol) in dichloromethane (50 ml). The reaction mixture was stirred at room temperature for 6 h. Then water was added carefully and the mixture was made alkaline with 1N NaOH to pH=9 and transferred to a separatory funnel. The organic phase was separated, dried over Na$_2$SO$_4$, and the solvent was removed by evaporation at reduced pressure. The residue thus obtained (4.4 g) was purified by flash chromatography using a mixture CHCl$_3$:MeOH=9:1 as eluent. 3 g of product were thus obtained, and were transformed into the corresponding hydrochloride by dissolution in ethanol, addition of hydrogen chloride in ethanol, evaporation of the solvent and crystallization from a mixture of ethyl acetate:ethanol 9:1, to give the desired product (2.8 g).

m.p.: 249-252° C.

Elemental analysis for $C_{22}H_{26}N_4O_2 \cdot HCl \frac{2}{3} H_2O$

|  | C | H | N |
|---|---|---|---|
| Found % | 62.14 | 6.64 | 13.45 |
| Calculated % | 61.91 | 6.69 | 13.13 |

$^1$H-NMR (δ, DMSO): 1.96-2.25 (m, 4H) 2.67-3.47 (m, 7H); 3.63 (d, J=12 Hz, 2H); 3.95 (s, 3H); 6.69-6.80 (m, 2H); 7.00-7.13 (m, 3H); 7.38 (t, J=9 Hz, 1H); 7.56 (d, J=9 Hz, 1H); 7.76 (d, J=9 Hz, 1H); 9.37 (s broad, 1H); 10.35-10.90 (m, 2H)

EXAMPLE 8

N((1-(2-(4-hydroxyphenyl)ethyl)-4-piperidinyl)methyl)-5-methyl-1-(1-methylethyl)-1H-indazole-3-carboxamide hydrochloride (AF3R296)

(I, $R_a=CH_3$, $R_{b=i-C_3}H_7$, $R_c=4$-OH, $R_d=H$, X=C(O)NHCH$_2$)

a) 1-(2-(4-hydroxyphenyl)ethyl)-4-piperidinyl-methane-amine

The title product was obtained (9.3 g) by working in a similar way to that described in Example 1b) but starting from the product of Example 1a) (7.5 g, 0.037 mol) and 2-(4-hydroxyphenyl)ethyl bromide (7.5 g; 0.037 mol), prepared as described in Acta Chemica Scandinava (1947-1973) 1967, 21 (1), 52-62, instead of from 2-(4-nitrophenyl)ethyl bromide.

$^1$H-NMR (δ, CDCl3+D2O): 1.15-1.41 (m, 3H); 1.74 (d, J=9 Hz, 2H); 1.90-2.07 (m, 2H); 2.45-2.61 (m, 4H); 2.65-2.75 (m, 2H); 3.01 (d, J=12 Hz, 2H); 6.75 (d, J=9 Hz, 2H); 7.00 (d, J=9 Hz, 2H).

b) isopropyl ester of 1(1-methylethyl)-5-methyl-1H-indazole-3-carboxylic acid

A 60% suspension of sodium iodide in mineral oil (17.1 g; 0.43 mol) was added to a suspension of 5-methyl-1H-indazole-3-carboxylic acid (30 g; 0.17 mol) prepared as described in J. Heterocyclic Chem. 1964, Vol. 1 (5) 239-241, in dimethylformamide (450 ml), and the reaction mixture was heated to 70° C. After 30 minutes, isopropyl bromide (48 ml, 0.51 mol) was added.

The reaction mixture was stirred for 6 hours at 70° C. After cooling, water was added. The reaction mixture was transferred to a separatory funnel and extracted with diethyl ether. The organic phase was washed with water saturate with sodium bicarbonate and, finally, the solvent was removed by evaporation at reduced pressure.

In this way 20 g of an oil were obtained, which were purified by flash chromatography, eluting with a mixture hexane:ethyl acetate=7:3, to give 12 g of the desired product.

$^1$H-NMR (δ, CDCl3): 1.47 (d, J=6 Hz, 6H); 1.64 (d, J=7 Hz, 6H); 2.50 (d, J=1 Hz, 3H); 4.92 (heptet, J=7 Hz, 1H); 5.39 (heptet, J=6 Hz, 1H); 7.23 (dd, J=9; 1 Hz, 1H); 7.40 (d, J=9 Hz, 1H); 7.95 (quintet, J=1 Hz, 1H).

c) 1-(1-methylethyl)-5-methyl-1H-indazole-3-carboxylic acid

A suspension of the product prepared according to Example 8b) (8 g; 0.03 mol) in 1M NaOH (42 ml) was heated under reflux for 3 hours. It was then poured into water, acidified with 2M HCl and extracted with dichloromethane. After evaporation of the solvent at reduced pressure, 7 g of the desired product were obtained.

$^1$H-NMR (δ, CDCl3): 1.61 (d J=7 Hz, 6H); 2.44 (s, 3H); 4.88 (heptet, J=7 Hz, 1H); 7.19 (d, J=9 Hz, 1H); 7.34 (d, J=9 Hz, 1H); 7.97 (s, 1H); 9.32 (s broad, 1H).

d) chloride of 1-(1-methylethyl)-5-methyl-1H-indazole-3-carboxylic acid

Thionyl chloride (6.78 g; 0.057 mol) was added to a suspension of the product prepared according to Example 8c) (4.01 g; 0.019 mol) in toluene (70 ml), and the reaction mixture was heated under reflux for 2 hours. The solvent was removed by evaporation at reduced pressure and taken up twice with toluene (50 ml×2) to give the desired product (4.3 g) which was used as such without further purification.

e) N((1-(2-(4-hydroxyphenyl)ethyl)-4-piperidinyl)methyl)-5-methyl-1-(1-methylethyl)-1H-indazole-3-carboxamide hydrochloride Working in a similar way to that described in Example 3 but using the product of Example 8a) (4.0 g, 0.017 mol) and the chloride of 1-(1-methylethyl)-5-methyl-1H-indazole-3-carboxylic acid (4.0 g, 0.017 mol), prepared as described in the preceding Example 8d), 4.5 g of the desired product were obtained, and this were transformed into the corresponding hydrochloride by dissolution in absolute ethanol, addition of hydrogen chloride in ethanol and recrystallization from ethanol to give the desired salt (3.2 g).

m.p.: 257.5-259.5° C.

Elemental analysis for $C_{26}H_{34}N_4O_2HCl$

|  | C | H | N |
|---|---|---|---|
| Found % | 66.20 | 7.75 | 11.87 |
| Calculated % | 66.30 | 7.49 | 11.89 |

$^1$H-NMR (δ, DMSO): 1.53 (d, J=7 Hz, 6H); 1.44-1.76 (m, 3H); 1.87 (d, J=12 Hz, 2H); 2.42 (s, 3H); 2.79-3.45 (m, 8H); 3.54 (d, J=12 Hz, 2H); 5.03 (heptet, J=7 Hz, 1H); 6.73 (d, J=9 Hz, 2H); 7.05 (d, J=9 Hz, 2H); 7.26 (d,d J=9.2 Hz, 1H); 7.67 (d, J=9 Hz; 1H); 7.96 (s, 1H); 8.30 (t, J=6 Hz, 1H); 9.35 (s, 1H); 10.35 (s broad, 1H),

TESTS

1. Mechanical Hyperalgesia Induced by CFA in the Rat

Male CD rats weighing 150-200 g on arrival were used. Using an analgesiometer, rats were selected having a response threshold to a mechanical nociceptive stimulus of from 150 to 180 g. By applying a gradual increase in pressure on the dorsal zone of the rat's left hind foot, the instrument makes it possible to record the nocifensive response, expressed in grams, corresponding to the moment when the animal retracts its foot [Randall L O and Semite J J. A method for the measurement of analgesic activity on inflamed tissue. Arch. Int. Pharmacodyn. Ther. 1957; 111: 409-419].

Hyperalgesia was induced by unilateral injection of 150 μl of Complete Freund's Adjuvant (CFA) in the plantar surface of the animal's left hind foot [Andrew D, Greenspan J D. Mechanical and heat sensitization of cutaneous nociceptors after peripheral inflammation in the rat. J Neurophysiol 1999; 82(5): 2649-2656; Hargreaves K, Dubner R, Brown R, Flores C, Joris J. A new and sensitive method for measuring thermal nociception in cutaneous hyperalgesia. Pain 1988; 32: 77-88].

The compounds under examination were tested (dose $10^{-5}$ mol/kg) by carrying out the test 23 hours after injection of CFA.

At 1 h following the treatment, the pain threshold measured in control animals was compared with that measured in animals treated with the product under examination. The control animals were treated with the same vehicle (water) used for administering the products under examination. The results are shown in Table 1.

TABLE 1

Effect on CFA

| Treatment | Number of rats | Pain threshold (g) 1 h after treatment |
|---|---|---|
| Vehicle | 12 | 121 ± 4.1 |
| AF3R294 | 12 | 194 ± 22.4 |
| AF3R296 | 12 | 151 ± 10.7 |
| AF3R298 | 12 | 174 ± 9.8 |
| AF3R302 | 12 | 160 ± 10.2 |
| AF3R306 | 12 | 186 ± 11.0 |
| AF3R328 | 12 | 150 ± 8.7 |
| AF3R330 | 12 | 161 ± 10.5 |
| AF3R334 | 12 | 170 ± 11.0 |

The pain threshold of normal animals of equal weight/age=155±2.1 g

2. Mechanical Hyperalgesia in Rats with Diabetes Induced by Streptozotocin

Male CD rats weighing 240-300 g on arrival were used.

Diabetic syndrome was induced by a single intraperitoneal (i.p.) injection of 80 mg/kg of streptozotocin dissolved in sterile physiological solution [Courteix C, Eschalier A, Lavarenne J. Streptozotocin-induced diabetic rats: behavioural evidence for a model of chronic pain. Pain, 1993; 53: 81-88; Bannon A W, Decker M W, Kim Dj, Campbell J E, Arneric S P. ABT-594, a novel cholinergic channel modulator, is efficacious in nerve ligation and diabetic neuropathy models of neuropathic pain. Brain Res. 1998; 801: 158-63].

After at least three weeks following the injection of streptozotocin, rats were selected having a level of glycaemia ≧300 mg/dl and having a response threshold to a mechanical nociceptive stimulus ≦120 g. The glycaemia levels were measured by means of a reflectometer using reactive strips impregnated with glucose oxidase. The pain threshold was measured using an analgesiometer. By applying a gradual increase in pressure on the dorsal zone of the rat's left hind foot, the instrument makes it possible to record the nocifensive response, expressed in grams, corresponding to the moment when the animal retracts its foot.

At 2 h following the treatment, the pain threshold measured in control animals was compared with that measured in animals treated with the product under examination (dose $10^{-5}$ mol/kg).

The control animals were treated with the same vehicle (water) used for administering the products under examination. The results are shown in Table 2.

TABLE 2

Effect on diabetic neuropathy

| Treatment | Number of rats | Pain threshold (g) 2 h after treatment |
|---|---|---|
| Vehicle | 8 | 112 ± 4.0 |
| AF3R294 | 8 | 198 ± 18.6 |
| AF3R296 | 8 | 154 ± 8.7 |
| AF3R298 | 8 | 170 ± 10.2 |
| AF3R302 | 8 | 164 ± 10.2 |
| AF3R306 | 8 | 184 ± 13.8 |
| AF3R328 | 8 | 158 ± 6.2 |
| AF3R330 | 8 | 171 ± 9.6 |
| AF3R334 | 8 | 184 ± 10.5 |

The pain threshold of normal animals of equal weight/age=240±8.7 g

What we claim is:

1. An intermediate of formula (II)

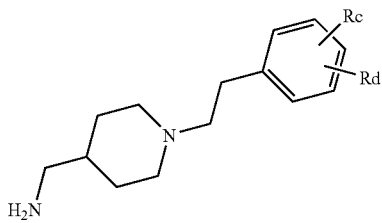

(II)

where
$R_c$ is hydroxy, amino, di-($C_1$-$C_3$)alkyl-amino, tri-($C_1$-$C_3$) alkyl-ammoniomethyl, nitro, trifluoromethyl, nitrile, $CH_3C(O)NH$, $CH_3SO_2NH$, $CH_3SO_2$, R'R"$NSO_2$, where R' and R" are H, or linear or branched $C_1$-$C_6$ alkyl, $R_d$ is H, hydroxy, amino, di-($C_1$-$C_3$)alkyl-amino, tri-($C_1$-$C_3$)alkylammoniomethyl, nitro, trifluoromethyl, nitrile, $CH_3C(O)NH$, $CH_3SO_2NH$, $CH_3SO_2$, R'R"$NSO_2$, where R' and R" are H, or linear or branched $C_1$-$C_6$ alkyl.

2. The intermediate of claim 1, wherein $R_c$ is a hydroxyl group.

3. The intermediate of claim 1, wherein $R_c$ is an amino group.

4. The intermediate of claim 1, wherein $R_c$ is a di-($C_1$-$C_3$) alkyl-amino group.

5. The intermediate of claim 1, wherein $R_c$ is a tri-($C_1$-$C_3$) alkyl-ammoniomethyl group.

6. The intermediate of claim 1, wherein $R_c$ is a nitro group.

7. The intermediate of claim 1, wherein $R_c$ is a trifluoromethyl group.

8. The intermediate of claim 1, wherein $R_c$ is a nitrile group.

9. The intermediate of claim 1, wherein $R_c$ is a $CH_3C(O)NH$ group.

10. The intermediate of claim 1, wherein $R_c$ is a $CH_3SO_2NH$ group.

11. The intermediate of claim 1, wherein $R_c$ is a $CH_3SO_2$ group.

12. The intermediate of claim 1, wherein $R_c$ is a R'R"$NSO_2$, where R' and R" are H, group.

13. The intermediate of claim 1, wherein $R_c$ is a linear $C_1$-$C_6$ alkyl group.

14. The intermediate of claim 1, wherein $R_c$ is a branched $C_1$-$C_6$ alkyl group.

15. The intermediate of claim 1, wherein $R_d$ is H.

16. The intermediate of claim 1, wherein $R_d$ is a hydroxyl group.

17. The intermediate of claim 1, wherein $R_d$ is an amino group.

18. The intermediate of claim 1, wherein $R_d$ is a di-($C_1$-$C_3$) alkyl-amino group.

19. The intermediate of claim 1, wherein $R_d$ is a tri-($C_1$-$C_3$)alkyl-ammoniomethyl group.

20. The intermediate of claim 1, wherein $R_d$ is a nitro group.

21. The intermediate of claim 1, wherein $R_d$ is a trifluoromethyl group.

22. The intermediate of claim 1, wherein $R_d$ is a nitrile group.

23. The intermediate of claim 1, wherein $R_d$ is a $CH_3C(O)NH$ group.

24. The intermediate of claim 1, wherein $R_d$ is a $CH_3SO_2NH$ group.

25. The intermediate of claim 1, wherein $R_d$ is a $CH_3SO_2$ group.

26. The intermediate of claim 1, wherein $R_d$ is a R'R"$NSO_2$, where R' and R" are H, group.

27. The intermediate of claim 1, wherein $R_d$ is a linear $C_1$-$C_6$ alkyl group.

28. The intermediate of claim 1, wherein $R_d$ is a branched $C_1$-$C_6$ alkyl group.

* * * * *